United States Patent [19]
Chang

[11] Patent Number: 5,275,820
[45] Date of Patent: Jan. 4, 1994

[54] STABLE SUSPENSION FORMULATIONS OF BIOERODIBLE POLYMER MATRIX MICROPARTICLES INCORPORATING DRUG LOADED ION EXCHANGE RESIN PARTICLES

[75] Inventor: Nienyuan J. Chang, Irvine, Calif.

[73] Assignee: Allergan, Inc., Irvine, Calif.

[21] Appl. No.: 634,500

[22] Filed: Dec. 27, 1990

[51] Int. Cl.$^5$ .................. A61K 9/16; A61K 9/58; A61K 9/10

[52] U.S. Cl. .................. 424/426; 424/428; 424/433; 424/434; 424/435; 424/436; 424/486; 424/497; 514/912; 514/913; 514/914; 514/772.1; 514/772.5; 514/772.6; 514/952; 427/3; 427/212

[58] Field of Search .......... 424/80, 79, 497, 426, 424/428, 457, 482, 78.1, 78.24; 514/912–915

[56] References Cited

U.S. PATENT DOCUMENTS

| | | | |
|---|---|---|---|
| 4,293,539 | 10/1981 | Ludwig et al. | 424/19 |
| 4,795,644 | 1/1989 | Zentner | 424/468 |
| 4,814,183 | 3/1989 | Zentner | 424/485 |
| 4,859,461 | 8/1989 | Chow et al. | 424/79 |
| 4,911,920 | 3/1990 | Jani et al. | 424/78 |
| 4,940,588 | 7/1990 | Sparks et al. | 424/490 |
| 4,948,580 | 8/1990 | Browning | 424/434 |
| 4,952,420 | 8/1990 | Sparks et al. | 424/419 |
| 4,983,392 | 1/1991 | Robinson | 424/428 |
| 4,996,047 | 2/1991 | Kelleher et al. | 424/79 |
| 5,071,646 | 12/1991 | Malkowska et al. | 424/497 |
| 5,100,668 | 3/1992 | Edelman et al. | 424/485 |

*Primary Examiner*—Edward Webman
*Attorney, Agent, or Firm*—Poms, Smith, Lande & Rose

[57] ABSTRACT

Sustained release pharmaceutical compound delivery compositions and methods for their production are disclosed wherein ion exchange resin particles are loaded with releasably bound pharmaceutical compounds prior to incorporation in an erodible polymeric matrix to form microparticulates. The microparticulates are suspended in a fluid medium where the encapsulating polymeric matrix shields the drug loaded ion exchange resin from solvent interaction. Administration to a target tissue site initiations erosion of the polymer matrix and release of the loaded pharmaceutical compound.

24 Claims, No Drawings

STABLE SUSPENSION FORMULATIONS OF BIOERODIBLE POLYMER MATRIX MICROPARTICLES INCORPORATING DRUG LOADED ION EXCHANGE RESIN PARTICLES

FIELD OF THE INVENTION

The present invention relates in general to sustained release pharmaceutical compound delivery systems. More particularly, the present invention is directed toward pharmaceutical drug delivery compositions having improved delivery characteristics and enhanced long-term storage stability, particularly when used in conjunction with hydrophilic pharmaceutical compounds in aqueous systems. The compositions of the present invention utilize liquid suspensions of erodible polymeric microparticulates or microcapsules incorporating smaller ion exchange resin particles which, prior to incorporation in the surrounding polymer matrix, have been loaded with one or more releasably bound pharmaceutical compounds.

BACKGROUND OF THE INVENTION

A common problem with the administration of many pharmaceutical compounds, including therapeutic and diagnostic drugs, has been the need to retain effective quantities of these compounds in contact with targeted tissue sites for sufficient periods of time to accomplish the desired therapeutic or diagnostic purpose. This problem is particularly acute in connection with physiological systems characterized by rapid fluid turnover or drainage. For example, in the ocular environment tear turnover and drainage through the lacrimal drainage system quickly remove the major portion of any pharmaceutical compound administered to the surface of the eye so that only a small fraction of the original dosage remains in contact with the ocular tissue for any period of time. Analogous problems are encountered in connection with the treatment of the nasal mucosa, oral and anal cavities, uro-genital track, vagina and similar physiologic environments.

Early approaches at addressing this problem generally relied upon the repeated administration of relatively large dosages of pharmaceutical compounds to compensate for the rapid loss of the compounds following their administration to the target site. Though relatively successful at maintaining effective concentrations of the desired pharmaceutical agents in contact with the target tissue such strategies were wasteful and had a number of drawbacks. These drawbacks included the expense associated with using relatively large quantities of pharmaceutical compounds, patient discomfort with repeated drug administration and systemic side-effects associated with large and frequent drug doses. Alternative approaches to the solution of this problem utilized viscous ointments and gels as delivery vehicles for the pharmaceutical compounds. These semi-solid delivery vehicles slowed down the rapid loss of the pharmaceutical compounds and retained an adequate dosage in contact with the target tissue. However, effectively delivering a controlled drug dosage with such widely variable systems proved difficult. Additionally, though satisfactory for direct topical application to mucous membranes, skin and the conjunctiva of the eye, such viscous delivery vehicles were not suitable for injection. More over, when utilized to treat ocular conditions such drug containing ointments and gels formed barriers to sight and produced an uncomfortable and aesthetically unpleasant crusting along the edges of the eyelids. These drawbacks as well as the possibility of blockage of the lacrimal duct when used to treat the eye lead to decreased patient acceptability and utilization of these systems.

A more modern approach directed at overcoming these problems has been the use of controlled or sustained release drug delivery systems. Typically, these systems utilize a polymeric matrix incorporating a therapeutic or diagnostic pharmaceutical compound. The polymer matrix is usually configured as a macroscopic insert designed to be placed in contact with the target tissue site. Once in position, the incorporated pharmaceutical compounds are released in a controlled manner through diffusion from the polymer matrix or in response to erosion of the polymer through mechanical or chemical means. Though generally effective, a significant disadvantage associated with such macroscopic controlled release inserts was the need for medical personnel to position and remove the devices. Additionally, patient discomfort with the inserted devices limited their use.

The subsequent development of microparticulate polymeric drug delivery vehicles addressed some of these problems. Once suspended in solutions of appropriate viscosities they were capable of either topical administration or administration through injection. Additionally, when properly formulated patients were able to self-administer such microparticulate suspensions in the form of drops or ointments. However, in spite of these successes significant problems remain with the administration and handling of microparticulate drug delivery vehicles. For example, fluid turnover or drainage at the target site may prematurely sweep the microparticulates from the target tissue along with the carrier liquid. This problem is particularly acute when microparticulate suspensions are administered as eye drops.

Further detracting from their utility, microparticulate drug delivery vehicles formed from water labile polymers must be stored in an anhydrous environment until just prior to use. Unless a liquid carrier other than water is used to suspend such microparticulates, the end user must suffer the inconvenience of combining the aqueous liquid carrier with the microparticulates immediately prior to administration. Though water labile erodible polymer microparticulates may be preferred because they do not require removal from the target site following administration, their inability to remain suspended in a ready-to-use formulation makes it virtually impossible to provide a pre-mixed water labile microparticulate drug delivery vehicle with even a minute shelf life.

Further compounding these problems, the therapeutic and diagnostic compounds that typically would be incorporated into such microparticulate delivery vehicles are often hydrophilic, water soluble, or even water reactive. As a result, during storage in aqueous suspension these pharmaceutical compounds will leach from the microparticulate carriers into the carrier solution where they may react with solvent molecules. This may result in a substantial loss of the desired pharmaceutical activity as well as directly impacting the ability to control the drug delivery rate from the suspension. Thus, depending upon the diffusion rate of the hydrophilic, water soluble or water reactive pharmaceutical compound involved, the available shelf life of a microparticulate suspension will be much shorter than even the minimum desirable shelf life.

In addition to the problems of shelf life and longterm storage instability, when hydrophilic, water soluble or water reactive pharmaceutical compounds are incorporated into polymeric drug delivery vehicles there is a significant problem in maintaining control of the actual drug delivery characteristics such as the drug release rate and the drug delivery duration. Undesirably fast delivery rates can result from a variety of factors including the extent of drug loading within the polymer matrix, polymer swelling, diffusion rate and erosion rate as well as the length of time the polymer has remained in suspension prior to administration at the target site. Premature delivery also decreases the duration of drug availability.

An alternative drug delivery suspension is disclosed in U.S. Pat. No. 4,911,920. This patent discloses a sustained release ophthalmic formulation for treating glaucoma without the unpleasant stinging sensation normally associated with compounds for lowering intraocular pressure. The disclosed formulation incorporates an active pharmaceutical compound held in suspension by a cationic exchange resin dispersed in an aqueous solution or gel of an anionic polymer. The formulation is compounded by dispersing the cationic exchange resin in water, adding the active component and then the anionic polymer. When administered to the eye as a pourable liquid, gel or salt the active ingredient held by the cationic exchange resin and the anionic polymer is released when the ions naturally present in the tear fluid compete with the bound active ingredient for sites on the polymer vehicle and ionic exchange resin.

While reportedly effective at reducing ocular discomfort, this formulation does not address the problems of shelf life and long-term storage stability. More specifically, because the molecules of the active component or drug are free to defuse in and out of the ion exchange resin while maintaining an equilibrium concentration in the aqueous medium they are subject to degradation. This particularly true with respect to water labile compounds. Moreover, the release characteristics of this drug delivery vehicle may be less than desirable in that substantially spontaneous dumping of the bound active ingredient may occur at the target site. Additionally, when formulated at sufficient viscosities to reduce losses through drainage and turnover the compounds may interfere with vision.

Accordingly, it is principal object of the present invention to provide a sustained release pharmaceutical drug delivery composition having improved delivery characteristics and enhanced long-term storage stability.

It is an additional object of the present invention to provide a pharmaceutical drug delivery composition that is particularly well suited for use with hydrophilic, water soluble or water reactive pharmaceutical compounds and which may be formulated as an aqueous suspension that can be stored for a significant period of time prior to use.

It is a further object of the present invention to provide a sustained release pharmaceutical drug delivery composition with bioadhesive properties which enhance its retention at the target site without significantly increasing its viscosity.

SUMMARY OF THE INVENTION

Generally stated, the present invention accomplishes the above-described objectives by providing a pharmaceutical drug delivery composition which shields the incorporated pharmaceutical compounds from the suspending solvent and thus improves both delivery characteristics, stability and resultant shelf life. The compositions are particularly well suited to the administration of hydrophilic, water soluble or water reactive pharmaceutical compounds when formulated as aqueous suspensions.

The compositions of the present invention are formulated as liquid suspensions of microparticulate drug delivery vehicles. The microparticulates in turn are formed of an erodible polymer matrix which incorporates one or more drug loaded ion exchange resin particles. As a result the drug loaded resin particles are partially or completely enclosed by the polymeric matrix of the microparticulate or microcapsule. This shields or locks the bound drug or drugs inside the ion exchange resin particles and prevents the bound compounds from leaching into the suspension medium during storage as long as the liquid suspension is substantially free from salt ions or other organic ions. The compositions are preferably formulated at a pH lower than approximately 4 or 5 to prevent premature polymer erosion prior to administration. As a result, unlike known microparticulate suspension drug delivery vehicles, the delivery compositions of the present invention remain stable during storage for significant periods of time.

When the delivery compositions of the present invention are administered to a targeted tissue site the relatively high pH typically encountered in physiological fluids initiates the erosion of the microparticulate or microcapsular polymer matrix. In the preferred embodiments of the present invention the polymeric matrix erodes through hydrolysis rather than deprotonation. This results in a slow exposure of the incorporated drug loaded ion exchange resin particles rather than a spontaneous dissolution of the polymer matrix over a relative short period of time. As a result, the pharmaceutical compounds bound to the incorporated ion exchange resin particles are released from the resin through exchange with the salt ions present in the surrounding physiological fluids in a gradual manner rather than spontaneously dumping an inappropriately large dosage. As those skilled in the art will appreciate, the unique ability of the delivery compositions of the present invention to lock pharmaceutical compounds inside ion exchange resin particles by coating the particles with an erodible polymer makes the delivery compositions particularly well suited for administering hydrophilic, water soluble or water reactive compounds. For the first time, these pharmaceutical compounds can be formulated into an aqueous suspension having a practical shelf life and desirable delivery characteristics without modifying the solubility of the pharmaceutical compounds themselves.

The polymeric matrix of the microparticulates or microcapsules is preferably formed from one or more erodible bioadhesive compounds. Once delivered to the target site the bioadhesive microparticulates or microcapsules will adhere to the tissue being treated and resist being swept from the target site by fluid turnover. This increases the drug delivery duration and residence time without significantly increasing the overall solution viscosity. Thus, bioadhesive delivery compositions produced in accordance with the teachings of the present invention are particularly well suited for administering pharmaceutical or diagnostic compounds through injection or as drops.

Further objects, features and advantages of the sustained release pharmaceutical compound delivery compositions of the present invention, as well as a better understanding thereof, will be afford to those skilled in the art from a consideration of the following detailed explanation of preferred exemplary embodiments thereof.

DETAILED DESCRIPTION OF EXEMPLARY EMBODIMENTS

The sustained release pharmaceutical compound delivery compositions of the present invention are intended for use in delivering pharmaceutical compounds to biological tissues and physiological systems, particularly those characterized by fluid turnover or drainage. Exemplary target sites include the conjunctival surface of the eye, the nasal mucosa, oral and anal cavities, uro-genital track, vagina and similar physiological environments.

In addition to effectively delivering and maintaining an appropriate dosage of therapeutic or diagnostic pharmaceutical compounds to the targeted tissue, the delivery compositions of the present invention are also configured to address a more practical problem—long-term storage stability and a practical shelf life for multidose drug delivery formulations.

The delivery compounds of the present invention are liquid suspensions which are well suited for administration through injection or as dropable liquids or liquid sprays. In the past, such liquid suspensions of pharmaceutical compounds exhibited an undesirable degree of instability. This instability required the use of exotic solvents or two component formulations which were mixed immediately prior to administration to prevent premature leaching of the pharmaceutical compounds into solution or inactivation of the pharmaceutical compounds through interaction with solvent molecules.

Unlike the prior art drug delivery systems, the liquid compositions of the present invention remain stable over long periods of time when formulated in multiple dose configurations. This results in a practical, real-world shelf life which cannot be obtained with comparable prior art delivery systems. The capacity to be formulated as a stable multi-dose configuration also imparts an added degree of "user friendliness" which encourages the self administration of the compounds of the present invention. What is more, in complete contrast to the teachings of the prior art, the sustained release pharmaceutical compound delivery compositions of the present invention exhibit this enhanced long-term storage stability in conjunction with improved drug delivery characteristics.

This previously unobtainable combination of properties is achieved without chemically modifying the therapeutic or diagnostic compounds to be delivered by the compositions. Rather, the pharmaceutical compounds are locked inside the pores of ion exchange resin particles, which are then embedded in a polymer matrix or polymeric microcapsule which prevents the pharmaceutical compounds from diffusing out of the resin until delivered to the target site. This locking away is accomplished by releasably binding the pharmaceutical compound or compounds to be delivered onto microscopic ion exchange resin particles. These loaded ion exchange resin particles are then incorporated into an erodible polymeric matrix or erodible polymeric microcapsule to form larger microparticulates. Preferably, the incorporating polymer matrix or capsule encloses, at least partially, one or more loaded ion exchange resin particles. The microparticulates so formed are then suspended in a substantially non-ionic liquid carrier medium to form the composition.

More specifically, the sustained release pharmaceutical compound delivery compositions of the present invention are generally formed as follows. First, one or more pharmaceutical compounds are reversibly loaded onto ion exchange resin particles. As well be appreciated by those skilled in the art, ion exchange resins are widely available from a variety of commercial sources for a broad range of applications. The commercial suppliers include Bio Rad, Dow Chemical, and Rohm and Haas. All commercially available ion exchange resins are contemplated as being within the scope of the present invention. Though the properties of the ion exchange resins may vary depending upon the intended application, they generally consist of an insoluble porous polymer lattice or matrix with attached ionic functional groups. However, the variable properties include the matrix structure, chemical type, functional group, degree of crosslinkage, ionic form and particle size. Exemplary ion exchange resins for practicing the present invention include crosslinked styrenedivinylbenzene lattice resins with either cationic or anion functional groups.

In the general ion exchange procedure, counterions such as $Na^+$, $Cl^-$ and $H^+$ are replaced by ionic forms of the desired pharmaceutical compounds which are, as a result, bound to the ionic functional group of exchange resin. This reversible binding is readily accomplished by mixing the pharmaceutical compounds of interest with the appropriate ion exchange resin in a suitable solvent as is known in the art and as will be discussed in detail below. However, broadly speaking, when the therapeutic or diagnostic pharmaceutical compound to be loaded on the porous ion exchange resin particle is basic or cationic in form, the exchange resin must be acidic. Preferably, for purposes of obtaining strong and prolong retention, the porous ion exchange resin is strongly acidic. For example, a suitable strongly acidic ion exchange resin will contain sulfonic acid exchange groups. Conversely, when the pharmaceutical compounds of interest are acidic or anionic, the exchange resin must be basic. Depending upon the strength of the ion exchange resin the pharmaceutical compounds of interest will be either weakly or strongly bound as desired. Additionally, it is also contemplated as being with in the scope of the present invention to utilize ion exchange resins formed from silicas and celluloses having sulfonic acid groups or, alternatively, carboxylic acid or quaternary ammonium salts as the reactive sites.

As an additional aspect of the present invention, the ion exchange resin particles are preferably sized on the order of 1 to 100 um in diameter. This produces a microparticulate which can easily pass through the lacrimal drainage system, if desired, and which also is readily dispersed in fluid suspension for drug loading purposes.

Similarly, a variety of exchange resin porosities may be utilized to practice the present invention. As those skilled in the art will appreciate, the pore size of the resin particle lattice should be sufficiently large to bind molecules of the size of the pharmaceutical compounds of choice. Additionally, as known in the art, the degree of porosity is directly related to the available surface area of the ion exchange resin particle. This, in conjunction with the number of reactive sites, will effect the amount of pharmaceutical compound which can be reversibly bound or loaded to the individual resin particles. Exemplary pore sizes range from approximately 10 angstroms to approximately 100 angstroms.

The drug delivery compositions of the present invention may be utilized to deliver virtually any pharmaceutical compound capable of binding to an ion exchange resin. For example, a variety of pharmaceutical compounds including antibacterials, antihistaminics, antiinflammatories, miotics, anticoloneurgics, mydriatics, antiglaucoma compounds, antiparisitic compounds, antivirals, carbonic anhydrase inhibitors, antifungal agents, and anesthetic agents, diagnostic agents, or immunosuppressive agents may be bound to the ion exchange resin particles. Specific exemplary pharmaceutical compounds include dipivalyl epinephrine, levobunolol, ofloxacin, 5-bromo-6-(imidazolin-2-ylamino)-quinoxaline, clonidine, pilocarpine, flurbiprofen, timolol, betaxolol, ibuprofen, acetaminophen, and their appropriate salt forms. However, these compounds are exemplary only and are not intended to limit the scope of the present invention.

It should be noted that the present invention is not limited to delivering individual pharmaceutical compounds. Combinations of pharmaceutical compounds bound to the appropriate ion exchange resins are contemplated as being within the scope of the present invention. Additionally, all resin particles need not be loaded to the same degree in order to practice the present invention. Thus, a variety of drug combinations, concentrations and resultant release rates may be incorporated into the drug delivery compositions of the present invention as desired. Exemplary drug loading concentrations will range from approximately 2% to 50%.

Once the ion exchange resin particles have been loaded with the releasably bound pharmaceutical compound or compounds of choice, the loaded resin particles are incorporated into an erodible polymeric matrix. The polymeric matrix coating incorporating the loaded ion exchange resin particle at least partially encloses the loaded exchange resin particle as either a solid matrix or enclosing microcapsule. Preferably, the polymeric matrix will totally enclose at least one or more of the drug loaded ion exchange resin particles. In this manner, the loaded pharmaceutical compound is locked into the ion exchange resin particle and shielded from external solvent effects. This shielding greatly facilitates the long-term storage of the loaded exchange resin particles. However, it should emphasized that completely enclosing the drug loaded ion exchange resin particle is not necessary to practice the present invention, although it is achievable by way of microcapsule preparation. Lesser degrees of enclosure simply reduce the completeness of the shielding or locking-in effect.

The polymeric matrix incorporating the drug loading ion exchange resin particles may be formed from any physiologically compatible erodible polymer known in the art. The polymers should be substantially non-ionic and soluble in the appropriate solvent to prevent displacement of the releasably bound pharmaceutical compounds from the loaded ion exchange resin particles. Preferred exemplary polymers include polyvinylpyrrolidone, poly(methylvinylether/maleic anhydride) and mixtures thereof.

Polyvinylpyrrolidone is a non-ionic water soluble polymer which has the additional benefit of being a bioadhesive. It is commercially available from a number of sources including GAF and Aldrich. Available in a wide range molecular weights ranging from 100,000 to 500,000, polyvinylpyrrolidone dissolves at varying rates depending upon its molecular weight, molecular weight distribution and morphology. During the dissolution process, the polymer initially forms a soft hydrogel which is capable of adhering to biological tissue. As the polymer absorbs additional water it dissolves into the surrounding aqueous system.

Similarly, poly(methylvinylether/maleic anhydride) is a non-ionic water soluble polymer having bioadhesive properties. Poly(methylvinylether/maleic anhydride) is available from GAF and other sources in a variety of molecular weights reportly ranging from 20,000 to 100,000. Upon contact with an aqueous medium, the anhydride functionalities of this copolymer hydrolyse to form acid functionalities. This initial hydrolysis leads to the formation of a polymeric soft hydrogel and, as hydrolysis proceeds, the copolymer becomes soluble in the surrounding aqueous medium. These properties are independent of molecular weight and, as a result, any of the readily available molecular weight copolymers are suitable for practicing the present invention.

It should be emphasized that while not essential to the present invention, bioadhesiveness is a particularly advantageous property of these exemplary polymeric materials. Utilizing a bioadhesive polymer to incorporate the loaded ion exchange resin particles gives the microparticulates the ability to adhere to biological tissue. This adhesive action ensures that the drug delivery composition is retained at the target site following administration in a safe and non-irritating manner. Moreover, this retention is accomplished without significantly increasing the viscosity of the delivery composition. This makes the delivery compositions of the present invention particularly well suited for delivering ophthalmic pharmaceuticals to the ocular environment as they resist lacrimal drainage without interfering with vision.

A preferred polymeric matrix may be formed from a polymer complex of poly(methylvinylether/maleic anhydride) and polyvinylpyrrolidone. When this exemplary composition is formulated at a pH lower than 4 to 5 the polymer complex is insoluble in aqueous solutions. Preferably, the ratio of poly (methylvinylether/maleic anhydride) to polyvinylpyrrolidone will range from approximately 1:1 to 4:1. Varying this ratio will alter the release rate from the drug delivery composition by modifying the erosion rate of the polymer. For example, a poly(methylvinylether/maleic anhydride) to polyvinylpyrrolidone ratio of approximately 3:1 produces the slowest release rate.

Incorporation of the loaded ion exchange resin particles into the polymer matrix may be accomplished through a variety of known methodologies including precipitation and phase coacervation techniques. These formation methodologies typically produce microparticulates of erodible polymeric matrix incorporating the smaller drug loaded ion exchange resin particles. Depending upon the size of the loaded resin particles, one or more of the particles may be incorporated into the larger microparticulate polymeric matrix. Following formation, the size of the microparticulates may be adjusted through milling or grinding as necessary to produce microparticulates preferably ranging in size from approximately 10 to 200 um in diameter. Though not essential, the preferred range of microparticulate sizing provides microparticles which may readily be suspended in solution to form single or multiple dose drug delivery suspensions.

Once sized to the desired dimension the loaded ion exchange resin incorporating polymeric microparticulates are suspended in a substantially non-ionic liquid medium or carrier. Suitable liquid carriers for practicing the present invention include those known in the art for carrying drugs to tissue sites. For example, aqueous based systems, hydrocarbon based systems, fluorocarbon based systems as well as silicone oils are known and used for such purposes. A preferred exemplary liquid suspension is deionized or substantially non-ionic water. This liquid carrier is inexpensive and readily compatible with the aqueous based physiology of the intended target tissue sites. To form the drug delivery composition of the present invention effective amounts of the microparticulates are simply dispersed in the desired solvent to form a suspension.

A preferred exemplary embodiment of the present invention utilizes a polymeric matrix formed from the polymer complex of poly(methylvinylether/maleic anhydride) and polyvinylpyrrolidone to incorporate the smaller drug loaded ion exchange resin particles, preferably a cationic exchange resin such as Bio-Rad AG5Dw-x8 or the like. These microparticles are then dispersed in deionized water to form a suspension and the pH is adjusted to approximately 3 to 4. At a system pH lower than approximately 4 to 5, this polymer complex is insoluble in water. Thus, the erodible bioadhesive polymer matrix locks the loaded pharmaceutical compounds inside the incorporated ionexchange resin particles. This prevents the pharmaceutical compounds from leaching out into the carrier medium as long as the aqueous solution is free from salt ions or any other organic ions. As a result, following preparation and suspension this exemplary embodiment of the present invention can be stored for extended periods of time. For example, preliminary experiments indicate that the delivery compositions of the present invention have a stable shelf life measured in months. Moreover, because of this ability to suspend the microparticulates in a liquid carrier for stable long-term storage, the delivery compositions can be prepared, stored and finally administered to a tissue site without additional handling by the patient. Thus, ready to use multiple packaging can be employed when preparing and administering these drug delivery vehicles through administration routes such as injection or as dropable liquids or sprays.

Once delivered to the targeted tissue site, the exemplary drug delivery compositions begin to erode when the encapsulating polymeric matrix is exposed to the higher pH present in physiological fluids. Unlike conventional enteric polymers whose water solubility or erodibility is pH sensitive, the exemplary polymer complex erodes through hydrolysis. This is a gradual process that results in the slow exposure of the releasably bound pharmaceutical compound loaded ion exchange resin particles incorporated in the larger microparticulates. Following exposure the releasably bound pharmaceutical compounds are released from the ion exchange resin as they are displaced from the ionic exchange sites by ions present in the physiological fluids. This results in a slow and gradual release of the loaded pharmaceutical compounds as opposed to the spontaneous drug dumping experienced by ion exchange resin carriers alone. As the preferred exemplary polymeric matrix erodes its bioadhesive properties assist in retaining the microparticulates at the target site thereby producing a sustained release pharmaceutical delivery.

As those skilled in the art will appreciate, by locking the pharmaceutical compounds away from the aqueous medium there is less potential for interaction between the pharmaceutical compounds and the carrier solvent or any other excipients in the formulation vehicle. Thus, the chemical stability of the pharmaceutical compounds is enhanced along with the storage stability of the delivery composition per se. This makes the exemplary delivery compositions particularly well suited for use in conjunction with hydrophilic, water soluble or water reactive pharmaceutical compounds. In accordance with the teachings of the present invention these compounds can be stably loaded into biologically compatible aqueous based delivery compositions which remain stable for significant periods of time producing practical shelf lives.

With this understanding in mind, the following examples are offered as being illustrative of the principles of the present invention and not by way of limitation.

EXAMPLE I

Preparation of Poly(methylvinylether/maleic anhydride) Polyvinylpyrrolidone Polymer Complex 2 g of poly(methylvinylether/maleic anhydride) (mw:67,000) were dissolved in 100 ml of acetonitrile (solution I). 1 g of polyvinylpyrrolidone (mw:40,000) was separately dissolved in 50 ml of acetonitrile (solution II). Solution II then was gradually added to solution I while being vigorously agitated. A precipitate formed instantly and was washed with acetonitrile four times before being dried in a vacuum oven. The dry matrix so produced was ground to fine particles (approximate diameter 30 um) with a ball mill.

As an alternative, 0.5 g of polyvinylpyrrolidone (mw: 80,000) was dissolved in 20 ml of acetonitrile to form solution I and 1.5 g of poly(methylvinylether/maleic anhydride) (mw:67,000) was dissolved separately in 30 ml of acetonitrile to form solution II. As before, the two solutions were mixed together with agitation. A white precipitate instantly formed, was dried and ground to 50 um particles with a mechanical grinder.

Different ratios of poly(methylvinylether/maleic anhydride) to polyvinylpyrrolidone ranging from 1:1 to 4:1 were repeated with the same protocol. Each time the matrix was successfully produced.

EXAMPLE II

Preparation of Sustained Release Delivery Composition 0.2 g of cationic ion-exchange resin (Bio-Rad AG50w-x8) was added to a 10 ml aqueous solution of levobunolol hydrochloride (2% w/v), and was allowed to equilibrate for 24 hours under mild stirring to load the ion exchange resin. The suspension was then filtered through 10 um filter paper to remove the loaded resin from the solution. The levobunolol hydrochloride concentration in the residual solution had dropped to 0.2% w/v indicating that 90% of the drug originally present was bound to the resin. The loaded resin, shielded from light, was dried in a vacuum oven for six hours before it was suspended in 50 ml of an acetonitrile solution of poly(methylvinylether/maleic anhydride) (6% w/v).

Separately, 1.5 g of polyvinylpyrrolidone (mw:22,000) was dissolved in 25 ml of acetonitrile and the resulting solution was added to the resin suspension with agitation. A white matrix precipitate, with resin particles embedded in it immediately formed. The precipitate was washed with acetonitrile as in Example I to remove any unbound levobunolol before being dried in a vacuum oven. The final content of levobunolol loaded resin incorporated into the polymeric matrix was determined to be 8.5 w/w %. The dried matrix was suspended in an aqueous suspension at pH 2 and sheared with a tissue homogenizer for 5 minutes. The resulting particle size was 500 um.

A pH stat experiment revealed that the erosion of the polymer matrix microparticlates took more than 10 hours at pH 9.5. At pH 7.4 and 37° C. in a phosphate buffer, the matrix particles yielded a duration of drug release of more than 6 hours.

EXAMPLE III

Preparation of Alternative Pharmaceutical Compound Delivery Composition 0.1 g of cationic ion-exchange resin (Bio-Rad AG50w-w16) was added to 3 ml of an aqueous solution of pilocarpine hydrochloride (5% w/v) and allowed to equilibrate for 24 hours under mild stirring to load the resin particles. The suspension was then filtered through 1.2 um filter paper to remove the resin from the solution. The pilocarpine hydrochloride concentration remaining in the solution had dropped to 1% w/v indicating that 80% of the drug originally present in solution was bound to the resin. The loaded resin was dried in a vacuum oven for six hours before being suspended in 20 ml of an acetone solution of poly(methylvinylether/maleic anhydride) (6% w/v, mw:22,000). Separately, 0.7 g of polyvinylpyrrolidone (mw:40,000) was dissolved in 20 ml of acetone and the resulting solution was added to the resin suspension with agitation. A polymer matrix precipitate incorporating the drug loaded resin particles immediately formed. The resin-embedded precipitate was then washed, dried, and ground to fine powder as in Example II.

In order to evaluate the long-term storage stability and shelf life of the sustained release pharmaceutical compound delivery compositions of the present invention the following experiments were conducted.

EXAMPLE IV

Storage Stability Testing of Levobunolol Delivery Composition

A copolymer matrix of poly(methyl vinyl ether/maleic anhydride)(mw:69,000) and polyvinylpyrrolidone (mw:54,000) in the ratio of 3:1 incorporating ion exchange resin particles loaded with releasably bound levobunolol was prepared as discussed in Example II. Each gram of the polymeric matrix contained approximately 0.1 gram of drug loaded resin particles having an average particle size of approximately 34 um. The drug loading of levobunolol hydrochloride was determined to be approximately 0.04 grams per gram of matrix. The polymeric matrix was ground through dry milling to a particle size of approximately 100 um and the resulting particles were dispersed in deionized water to form a 5% solid suspension. Following dispersion the pH of the aqueous suspension was adjusted to 4.1.

To determine the storage stability of the pharmaceutical compound delivery composition so produced the aqueous suspension was stored at 37° C. for a period of three months. Following storage a portion of the suspension was analyzed to determine the level of free levobunolol hydrochloride in the aqueous suspension medium. It was found to be less than 2%. It was also observed that the delivery composition evidenced no change in physical appearance other than a slight swelling of the microparticulates to approximately 150 um.

Following storage a portion of the sample was subjected to a USP in vitro dissolution study at 37° C. in phosphate buffer. The duration of drug release was determined to be greater than 5 hours with a $T_{50}$ of 1 hour and 20 minutes. The recovery of the drug was 98.7%.

As those skilled in the art will appreciate, additional preservatives and excipients can be added to the drug delivery compositions of the present invention within the scope and teachings thereof. An exemplary composition incorporating a nonionic preservative and unbound pharmaceutical compound in the suspension medium was formulated and subjected to long-term storage analysis as follows.

EXAMPLE V

Preparation of Alternative Composition

A copolymer matrix of poly(methylvinylether/maleic anhydride)(mw:69,000) and polyvinylpyrrolidone (mw:40,000) in the ratio of 3:1 embedded with pilocarpine hydrochloride loaded ion exchange resin particles was prepared as in Example II. Each gram of the polymeric matrix was determined to contain approximately 0.22 grams of drug loaded resin particles, each particle having an average size of approximately 34 um. The amount of pilocarpine hydrochloride per gram of polymeric matrix was determined to be approximately 0.13 gram per gram of matrix. The polymeric matrix incorporating the drug loaded resin particles was ground through a dry milling process to a particle size of approximately 150 um. The microparticulates so produced were suspended in deionized water to form an 8% solid suspension. To this suspension was added a nonionic preservative, chlorobutanal, at a concentration of 0.5%. To 100 mL of this solution was added 0.1 gram of free pilocarpine hydrochloride. The pH of this solution was adjusted to 3.9. The free pilocarpine hydrochloride concentration was determined to be 0.1%.

A sample of this solution was stored at 37° C. for a period of eight months. Following storage a portion of the sample was analyzed to determine the free pilocarpine hydrochloride concentration of the suspension. Analysis indicated that the concentration was 0.098%.

In closing, it should be understood that the embodiments of the present invention disclosed herein are illustrative of the principles of the present invention and that other modifications may be employed which are within the scope thereof. For example, erodible polymeric microcapsules incorporating drug loaded ion exchange resin particulates may be formed by suspending the loaded exchange resin particles in an emulsion of the polymeric solutions. Accordingly the present invention is not limited to that precisely as disclosed and described and is limited only by the appended claims.

I claim:

1. A sustained release pharmaceutical compound delivery composition having improved delivery characteristics and enhance long-term storage stability, said composition comprising:

a non-ionic liquid suspension of microparticulates, said microparticulates formed of an erodible bioadhesive polymeric matrix of poly and polyvinylpyrrolidone wherein the ratio of poly (methylvinylether/maleic anhydride) to polyvinylpyrrolidone ranges from approximately 1:1 to 4:1 by weight, incorporating at least one ion exchange resin particle sized from approximately 1 μm to 100 μm, said ion exchange resin particle having approximately 2 to 50 wt % of a pharmaceutical compound releasably bound thereto.

2. The sustained release pharmaceutical compound delivery composition of claim 1 wherein said liquid is water having a pH less than about 5.

3. The sustained release pharmaceutical compound delivery composition of claim 1 wherein the ratio of poly(methylvinylether/maleic anhydride) to polyvinylpyrrolidone is approximately 3:1 by weight.

4. The sustained release pharmaceutical compound delivery composition of claim 1 wherein each of said microparticulates is sized from about 10 um to about 500 um.

5. The sustained release pharmaceutical compound delivery composition of claim 1 wherein each of said ion exchange resin particle has a pore size ranging from about 10 angstroms to about 100 angstroms.

6. The sustained release pharmaceutical compound delivery composition of claim 1 wherein said ion exchange resin particle is selected from the group consisting of cation exchange resin particles, anion exchange resin particles, and combinations thereof.

7. The sustained release pharmaceutical compound delivery composition of claim 6 wherein said cation exchange resin particles include at least one exchange functionality selected from the group consisting of sulfonic acid and carboxylic acid.

8. The sustained released pharmaceutical compound delivery composition of claim 1 wherein said releasably bound pharmaceutical compound is selected from a group consisting antibacterials, antiinflammatories, miotics, anticholinergics, antiglaucoma compounds, antivirals, carbonic anhydrase inhibitors, aesthetic agents, diagnostic agents, and immunosuppressive agents.

9. The sustained release pharmaceutical compound delivery composition of claim 1 wherein said releasably bound pharmaceutical compound in selected from the group consisting of mydriatics, antihistaminics, and antiparasitic compounds.

10. The sustained release pharmaceutical compound delivery composition of claim 1 wherein said releasably bound pharmaceutical compound is selected from the group consisting of dipivalyl epinephrine, levobunolol, ofloxacin, 5-bromo-6-(imidazolin-2-ylamino)-quinoxaline, clonidine, pilocarpine, flurbiprofen, timolol, betaxolol, ibuprofen, and acetaminophen.

11. A sustained release aqueous pharmaceutical compound delivery composition having improved delivery characteristics and enhanced long term storage ability, said composition comprising:
a nonionic aqueous suspension of microparticulates, said aqueous suspension having a pH value of less than about 5, and said microparticulates formed of a bioerodible, bioadhesive polymeric matrix of poly(methylvinylether/maleic anhydride) and polyvinylpyrrolidone wherein the ratio of poly (methylvinylether/maleic anhydride) to polyvinylpyrrolidone ranges from approximately 1:1 to 4:1 by weight, incorporating at least one ion exchange resin particle sized from approximately 1 μm to 100 μm, said ion exchange resin particle having from 2 to 50 wt % of a pharmaceutical compound releasably bound thereto.

12. The sustained release pharmaceutical compound delivery composition of claim 11 wherein the ratio of poly(methylvinylether/maleic anhydride) to polyvinylpyrrolidone is approximately 3:1 by weight.

13. The sustained release pharmaceutical compound delivery composition of claim 11 wherein each of said microparticulates is sized from about 10 um to about 500 um.

14. The sustained release pharmaceutical compound delivery composition of claim 11 wherein each said ion exchange resin particles has a pore size ranging from about 10 angstroms to about 100 angstroms.

15. The sustained release pharmaceutical compound delivery composition of claim 11 wherein said ion exchange resin particle is selected from the group consisting of cation exchange resin particles, anion exchange resin particles, and combinations thereof.

16. The sustained release pharmaceutical compound delivery composition of claim 15 wherein said cation exchange resin particles include at least one exchange functionality selected from the group consisting of sulfonic acid and carboxylic acid.

17. The sustained release pharmaceutical compound delivery composition of claim 11 wherein said releasably bound pharmaceutical compound is selected from the group consisting of antibacterials, antiinflammatories, miotics, anticholinergics, antiglaucoma compounds, antivirals, carbonic anhydrase inhibitors, anitfungal agents, anesthetic agents, diagnostic agents, and immunosuppressive agents.

18. The sustained released pharmaceutical compound delivery composition of claim 11 wherein said releasably bound pharmaceutical compound is selected from the group consisting of mydriatics, antihistaminics, and antiparasitic compounds.

19. The sustained release pharmaceutical compound delivery composition of claim 11 wherein said releasably bound pharmaceutical compound is selected from the group consisting of dipivalyl epinephrine, levobunolol, ofloxacin, 5-bromo-6-(imidazolin-2-ylamino)-quinoxaline, clonidine, pilocarpine, flurbiprofen, timolol, betaxolol, ibuprofen, and acetaminophen.

20. A process for forming a sustained release pharmaceutical compound delivery composition having improved delivery characteristics and enhanced long term storage stability, said process comprising the steps of:
reversibly loading at least one ion exchange resin particles sized form approximately 1 μm to 100 μm with from approximately 2 to 50 wt % of at least one pharmaceutical compound;
incorporating said loaded ion exchange resin particle into an erodible polymeric matrix formed of poly(methylvinylether/maleic anhydride) and polyvinylpyrrolidone wherein the ratio of poly(methylvinylether/maleic anhydride) to polyvinylpyrrolidone ranges from approximately 1:1 to 4:1 by weight; and
suspending said erodible polymeric matrix incorporating said loaded ion exchange resin particle in a nonionic aqueous solution having a pH value of less than about 5.

21. The process of claim 20 wherein said loaded ion exchange resin particles is incorporated into said erodible polymeric matrix through the additional steps of:

suspending said loaded ion exchange resin particle in a solution of poly(methylvinylether/maleic anhydride); and adding a solution of polyvinylpyrrolidone thereto to form an erodible polymeric matrix precipitate incorporating said loaded ion exchange resin particle.

22. The process of claim 20 wherein said releasably bound pharmaceutical compound is selected from the group consisting of antibacterials, antiinflammatories, miotics, anticholinergics, antiglaucoma compounds, antivirals, carbonic anhydrase inhibitors, antifungal agents, anesthetic agents, diagnostic agents, and immunosuppressive agents.

23. The process of claim 20 wherein said releasably bound pharmaceutical compound is selected from the group consisting mydriatics, antihistaminics, and antiparasitic compounds.

24. The process of claim 20 wherein said releasably bound pharmaceutical compound is selected from the group consisting of dipivalyl epinephrine, levobunolol, ofloxacin, 5-bromo-6-(imidazolin-2-ylamino)-quinoxaline, clonidine, pilocarpine, flurbiprofen, timolol, betaxolol, and acetaminophen.

* * * * *

UNITED STATES PATENT AND TRADEMARK OFFICE
CERTIFICATE OF CORRECTION

PATENT NO. : 5,275,820
DATED : Jan. 4, 1994
INVENTOR(S) : Nienyuan J. Chang

It is certified that error appears in the above-indentified patent and that said Letters Patent is hereby corrected as shown below:

Column 13, line 3; after "poly" insert --(methylvinylether/maleic anhydride)--

Signed and Sealed this

Sixteenth Day of April, 1996

*Attest:*

BRUCE LEHMAN

*Attesting Officer*     Commissioner of Patents and Trademarks